(12) United States Patent
Ferree

(10) Patent No.: US 6,981,991 B2
(45) Date of Patent: Jan. 3, 2006

(54) ARTHROPLASTY DEVICES CONFIGURED TO REDUCE SHEAR STRESS

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 0 days.

(21) Appl. No.: 10/608,616

(22) Filed: Jun. 27, 2003

(65) Prior Publication Data

US 2004/0019386 A1 Jan. 29, 2004

Related U.S. Application Data

(60) Provisional application No. 60/392,234, filed on Jun. 27, 2002.

(51) Int. Cl.
*A61F 2/36* (2006.01)

(52) U.S. Cl. .................. 623/23.46; 623/23.15; 623/23.23

(58) Field of Classification Search ... 623/23.11–23.25, 623/22.42–22.46, 20.14–20.17, 20.26, 20.27, 623/20.29, 19.11, 19.14, 20.32, 20.35, 20.36, 623/20.28, 20.33, 22.4

See application file for complete search history.

(56) References Cited

U.S. PATENT DOCUMENTS

| | | | | |
|---|---|---|---|---|
| 5,507,817 A | * | 4/1996 | Craig et al. ............... | 623/20.11 |
| 5,653,765 A | * | 8/1997 | McTighe et al. .......... | 623/22.42 |
| 5,902,340 A | * | 5/1999 | White et al. ................ | 128/898 |
| 5,976,188 A | * | 11/1999 | Dextradeur et al. ...... | 623/23.23 |
| 6,139,580 A | * | 10/2000 | Wurzinger et al. ....... | 623/20.26 |
| 6,210,444 B1 | * | 4/2001 | Webster et al. ........... | 623/20.33 |
| 6,214,053 B1 | * | 4/2001 | Ling et al. ................ | 623/23.11 |
| 6,241,772 B1 | * | 6/2001 | Mackwood Ling et al. | 623/23.15 |
| 6,319,286 B1 | * | 11/2001 | Fernandez et al. ........ | 623/23.18 |
| 6,506,215 B1 | * | 1/2003 | Letot et al. ............... | 623/20.29 |
| 6,613,092 B1 | * | 9/2003 | Kana et al. ............... | 623/20.15 |
| 6,669,728 B2 | * | 12/2003 | Despres et al. ........... | 623/16.11 |
| 6,723,129 B2 | * | 4/2004 | Dwyer et al. ............. | 623/22.42 |
| 2002/0040244 A1 | * | 4/2002 | Despres et al. ........... | 623/22.15 |
| 2002/0111692 A1 | * | 8/2002 | Ralph et al. .............. | 623/23.17 |
| 2003/0065397 A1 | * | 4/2003 | Hanssen et al. .......... | 623/20.32 |
| 2003/0171816 A1 | * | 9/2003 | Scifert et al. ............. | 623/22.12 |
| 2004/0024471 A1 | * | 2/2004 | Ferree ....................... | 623/23.63 |
| 2004/0172139 A1 | * | 9/2004 | Dwyer et al. ............. | 623/22.43 |
| 2004/0243248 A1 | * | 12/2004 | Despres et al. ........... | 623/22.42 |
| 2005/0004679 A1 | * | 1/2005 | Sederholm et al. ....... | 623/22.42 |

FOREIGN PATENT DOCUMENTS

| JP | 2004202232 | * | 7/2004 |
|---|---|---|---|
| JP | 2004202234 | * | 7/2004 |

* cited by examiner

Primary Examiner—Alvin Stewart
(74) Attorney, Agent, or Firm—Jerrold J. Litzinger

(57) ABSTRACT

Arthroplasty devices having improved bone in growth to provide a more secure connection within the body. Different embodiments disclosed include devices having threaded intramedullary components, devices configured to receive bone growth promoting substances, devices with resorbable components, and devices configured to reduce shear stress.

12 Claims, 20 Drawing Sheets

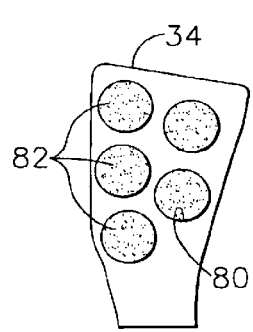
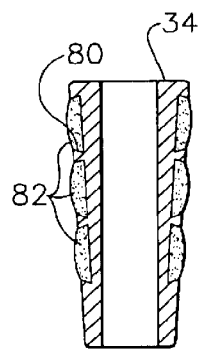
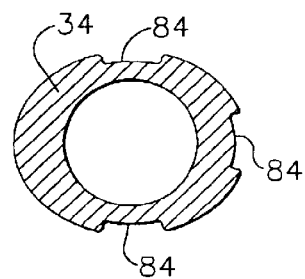
FIG. 9A　　　FIG. 9B　　　FIG. 9C
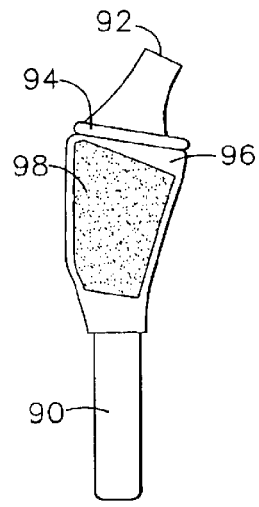
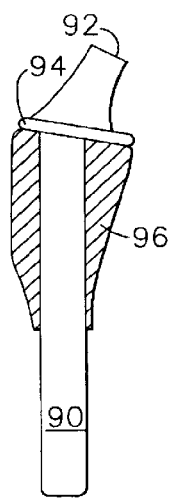
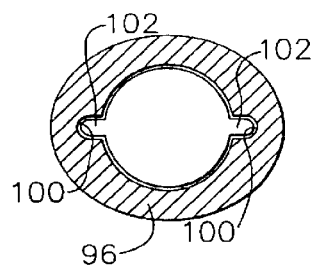
FIG. 10A　　　FIG. 10B　　　FIG. 10C

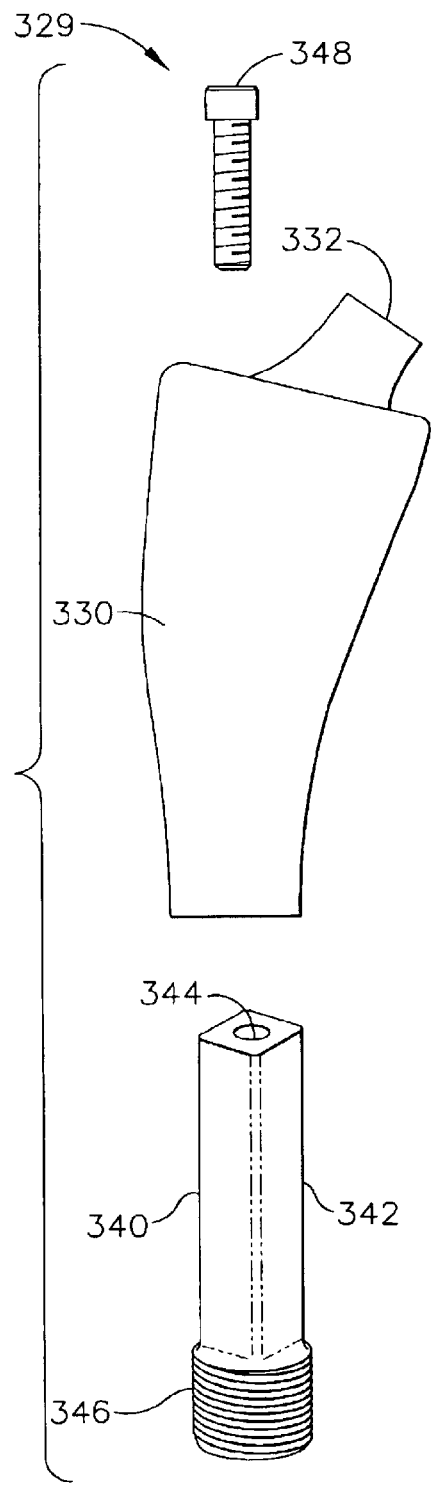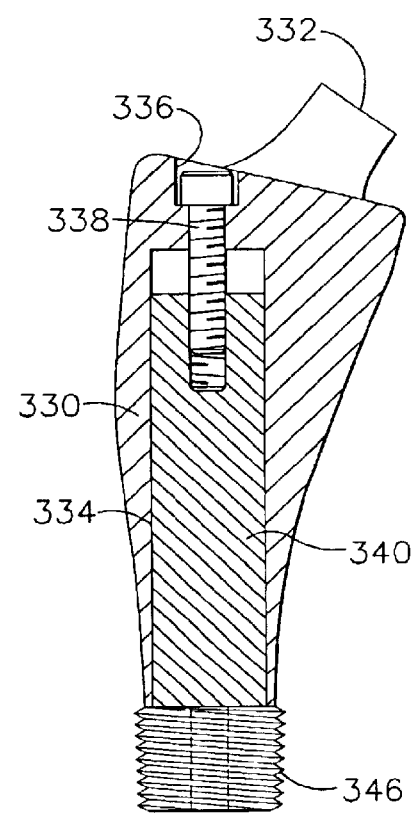
FIG. 24A
FIG. 24B

US 6,981,991 B2

ARTHROPLASTY DEVICES CONFIGURED TO REDUCE SHEAR STRESS

CROSS REFERENCE TO RELATED APPLICATIONS

This application claims benefit from U.S. Provisional Patent Application Ser. No. 60/392,234, filed Jun. 27, 2002, which application is incorporated herein by reference.

BACKGROUND OF THE INVENTION

1. Field of the Invention

The present invention is directed in general to arthroplasty devices and, in particular, to arthroplasty devices which improve bone growth into said devices.

2. Description of the Related Art

The use of arthroplasty devices to replace damaged or defective joints within the body is commonplace in the medical field. The prosthetic replacement of joints has evolved over the years from early relatively crude models to current prostheses which closely replicate functions and motions of a natural joint. Prosthetic arthroplasty devices have been used as replacements for the shoulder, hips, knee, ankle and invertebral disc.

One problem encountered with prosthetic joints includes movement of the implant with respect to the patient's bones. This motion often compromises fixation. Another problem that occurs is an abnormal stress transference from the implant to the bone.

The most common method of holding the implant in the bones is "press-fitting" the device into the intramedullary cavity of the bone. This often causes abnormal stress distribution, leading to premature failure.

These devices also rely on the ingrowth of the patient's bone to hold these devices in place. The difficulty of achieving true growth of a patient's bone into a metal prosthesis is a well known problem in the surgical field.

SUMMARY OF THE INVENTION

It is, therefore, an object of the present invention to provide an arthroplasty device which has improved bone ingrowth capabilities.

It is a further object of the present invention to provide an arthroplasty device configured to reduce shear stress.

It is a still further object of the present invention to provide an arthroplasty device having a resorbable component which restricts motion in a joint for a period of time to allow for improved bone ingrowth.

It is a still further object of the present invention to provide an arthroplasty device configured to receive bone growth promoting substances.

These and other objects and advantages of the present invention will be readily apparent in the description that follows.

BRIEF DESCRIPTION OF THE DRAWINGS

FIG. 9A is a lateral view of another embodiment of the present invention;

FIG. 9B is a cross-sectional view of the device of FIG. 9A;

FIG. 9C is a cross-sectional view of another version of the device of FIG. 9A;

FIG. 10A is a lateral view of another embodiment of the present invention;

FIG. 10B is a cross-sectional view of the device of FIG. 10A;

FIG. 10C is a different cross-sectional view of the device of FIG. 10A;

FIG. 24A is an exploded view of an alternative embodiment of a device according to the present invention;

FIG. 24B is a cross-sectional view of the device of FIG. 24A in the assembled position;

DETAILED DESCRIPTION OF THE EMBODIMENTS

Figure 1:
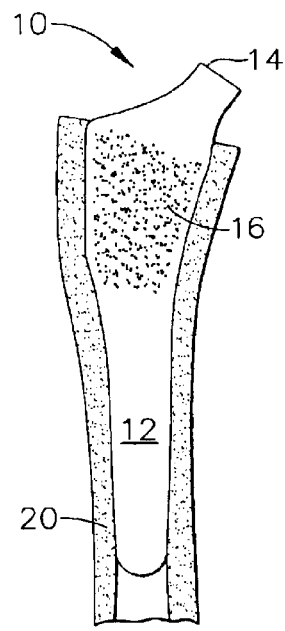
FIG. 1 is a lateral view, partly in cross section, of a femur and a prior art impacted femoral component of a hip replacement.

FIG 1. represents a typical prior art impacted femoral component of a hip replacement commonly used in the surgical field today. Referring now to FIG. 1, there is shown a femoral component 10 having an elongated tapered portion 12, an extended stem portion 14 for connecting component 10 to the prosthetic femoral head, and a textured surface area 16. In use, tapered portion 12 is driven into a femur 20 which has been prepared to receive component 10. Surface area 16 of component 10 is configured to encourage bone ingrowth to assist in the permanent attachment of component 10 within femur 20. Surface area 16 may contain small beads, fibrillar wires or other structures known in the art to promote bone ingrowth. This type of arthroplasty device relies on impaction of the device into patients' bones for stability.

Figure 2:
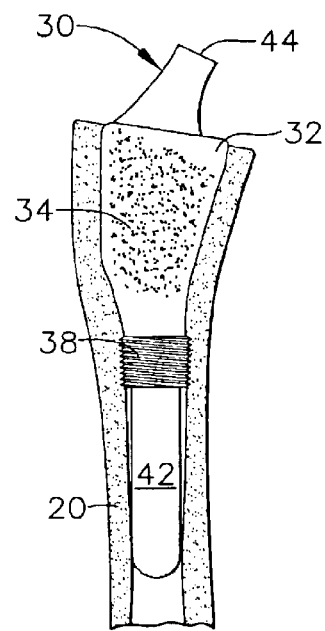
FIG. 2 is a lateral view, partly in cross section, of a femur and an embodiment of the present invention showing a femoral hip replacement device having a threaded component.
Figure 3:
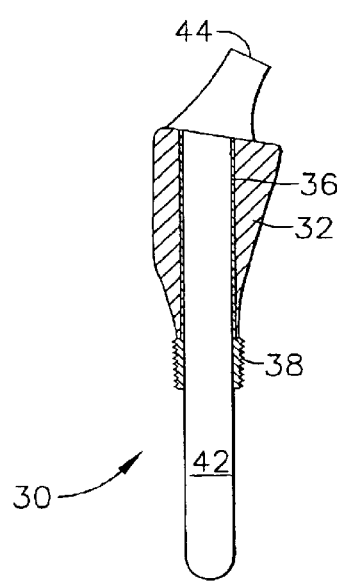
FIG. 3 is a cross-sectional view of the embodiment of the present invention shown in FIG. 2.
Figure 4:
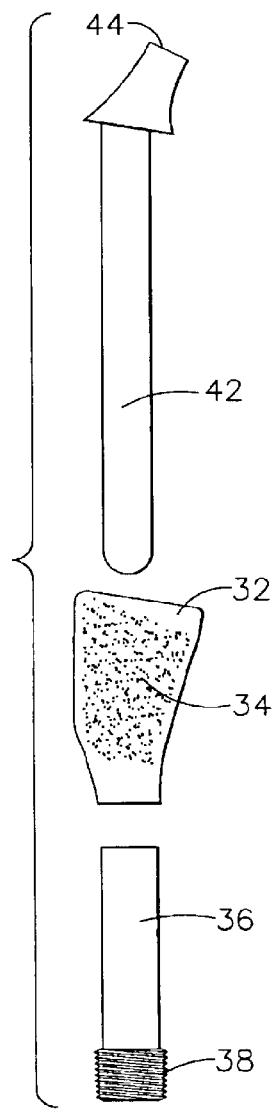
FIG. 4 is an exploded view of the device of FIG. 2.

The difficulty of achieving true growth of a patient's bone into metal prostheses is well known in the medical field. FIGS. 2–4 show a device according to the present invention which assists in overcoming this problem. Femoral hip replacement device, generally designated as 30, includes an upper outer sleeve 32 which contains a textured surface area 34, a tubular inner component 36 having a threaded lower portion 38, and an elongated rod component 42 having an outwardly extending stem 44. In operation, threaded portion 38 of component 36 engages an internally threaded area which has been previously incorporated into femur 20. Alternatively, portion 38 may contain self tapping threads for attachment within femur 20. Sleeve 32 is then installed on the tubular portion of component 36 such that it is held against threaded portion 38 and the inner walls of femur 20. Elongated rod component 42 is then inserted through tubular component 36 such that it is tightly held in place by sleeve 32 and femur 20, as can be best seen in FIG. 2.

Although device 30 contains surface area 34 to assist bone ingrowth, threaded section 38 helps to stabilize device 30, as threaded components are less likely to allow motion between the device and bone. Bone ingrowth, which is dependent upon the surface features of the device and motion between the device and the bone, is thus facilitated by decreasing motion between the arthroplasty device and a patient's bone.

Figure 5A:
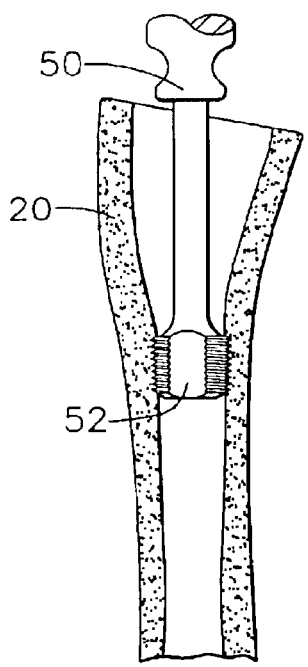
FIGS. 5A–D, taken together, show the sequence of installation of the device of FIG. 2.
Figure 5B:
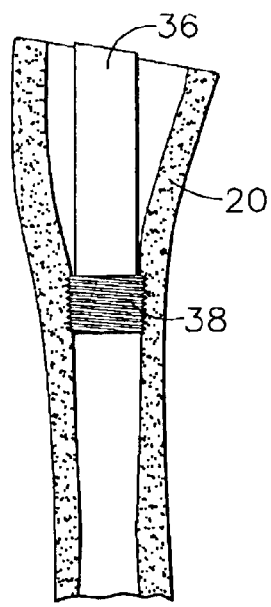
Figure 5C:
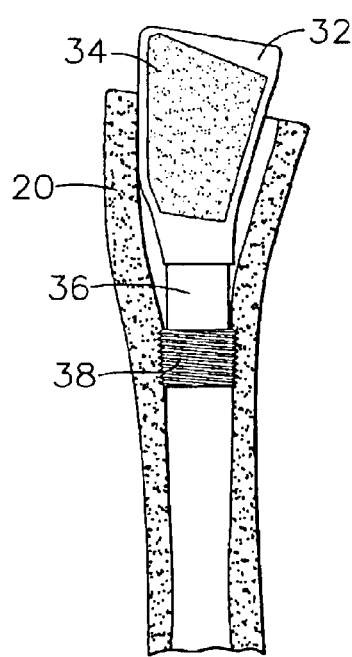
Figure 5D:
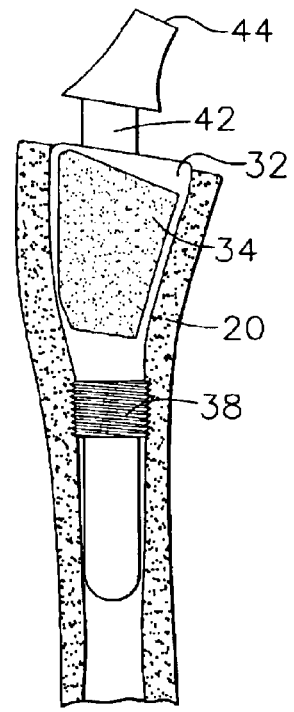

The process for installing device 30 is shown in FIGS. 5A–D. Referring now to FIG. 5A, a tap 50 having a thread cutting end 52 is used to chase threads within femur 20 in the area in which threaded portion 38 of component 36 is to be affixed within femur 20. Alternatively, portion 38 may be manufactured as a self-tapping device. After this has been performed, portion 38 is brought into threaded engagement with femur 20, with tubular portion 36 positioned above the threaded connection (FIG. sleeve 5B). Next, outer sleeve 32 is forced over tubular portion 36 until the edge of sleeve 32 contacts threaded portion 38 (FIG. 5C). Finally, elongated rod component 42 is inserted through tubular portion 36 captured within sleeve 32 such that outwardly extending stem 44 is properly positioned for attachment within the prosthetic femoral head. This construction decreases the possibility of motion between device 30 and femur 20, potentially enhancing bone ingrowth.

Figure 6:
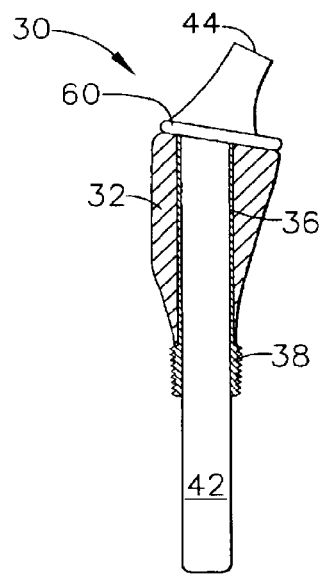
FIG. 6 is a lateral view, partly in cross section, of the device of FIG. 2 which includes a collared rod component.

FIG. 6 represents another embodiment of device 30 which a collar 60 positioned on rod component 42 between stem 44 and sleeve 32 to aid in the positioning of device 30 within femur 20. In this embodiment, rod component 42 is inserted through tubular portion 36 within sleeve 32 until collar 60 contacts sleeve 32. In this manner, forces within rod component 42 are transferred to sleeve 32 having textured surface 34 for bone ingrowth, adding additional stability to device 30.

Figure 7:
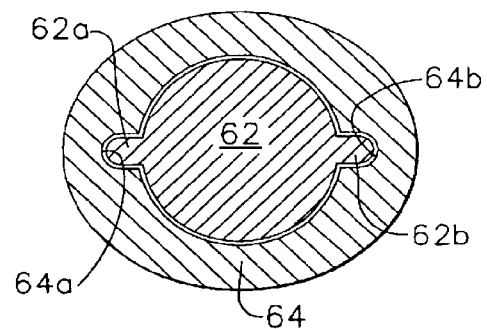
FIG. 7 is a cross-sectional view of the device of FIG. 2 which includes an anti-rotation feature.

FIG. 7 is a sectional view of an alternative embodiment of device 30 which adds an anti-rotation feature for additional stability. Referring now to FIG. 7, rod component 62 contains outwardly extending edges 62a, 62b. Tubular component 64 contains a pair of channels 64a, 64b within its inner walls corresponding to edges 62a, 62b. In this manner, rod component 62 cannot rotate within tubular component 64, adding additional stability to the arthroplasty device, which potentially promotes bone ingrowth. Rod component 62 may also contain a cruciform shape, with tubular component 64 having a corresponding shape.

Square threads, buttress threads, or reverse buttress threads may be used in the embodiments requiring threaded devices, as these decrease hoop stress on the bone. Hoop stress can lead to fracture of the bone. Taper threads may also be used. In addition, the threads can be either left or right handed.

Figure 8A:
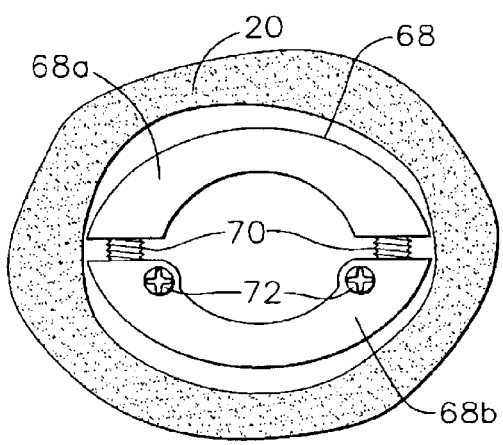
FIG. 8A is a cross-sectional view of the femur and another embodiment of the device of the present invention having an expandable component shown in the contracted position.
Figure 8B:
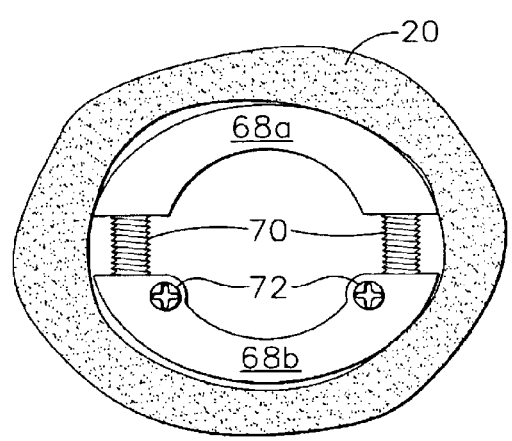
FIG. 8B is a cross-sectional view of the device of FIG. 8A showing the expandable component in the extended position.

FIGS. 8A–B represent another alternative embodiment for an arthroplasty device according to the present invention.

In this embodiment, an adjustable component 68 having a first section 68a and a second section 68b which are movable relative to each other by a pair of adjusting screws 70 is inserted into femur 20 in order to fit a patient's bone anatomy better. Screws 70 are adjustable to shift component 68 between a contracted position (FIG. 8A) and an expanded position (FIG. 8B). Screws 70 are adjusted by a corresponding pair of screws 72 which, when turned, control the adjusting motion provided by screws 70. Alternatively, a wrench may be used to turn a screw, or gear, which cooperates with a toothed component to force sections 68a and 68b apart.

Component 68 is placed into the intramedullary canal of a bone and expanded. The tighter fit provided by component 68 decreases motion between the prosthesis and the patient's bone. Adjustable component 68 also allows for compaction of the cancellous bone with the cortical bone into which the prosthesis device is inserted. Cancellous bone is rich in cells that promote bone ingrowth. Prior art impacted devices are generally inserted into the cortical bone after the removal of most of the cancellous bone. Thus, expanding components such as component 68 will aid in the immobilization of the prosthesis and preserve the healing characteristics of cancellous bone. While the device shown in FIGS. 8A–B show expansion of one component in one direction, multiple components may be used that expand in multiple directions. A torque wrench may be used to control the force and help prevent fracture of the bone into which the device is to be inserted. In addition, shape memory materials may be used to change the shape of components within the device. For example, a sleeve made of nitinol could be inserted in its contracted shape and then open to the expanded shape after insertion into the base.

Alternative expansion mechanisms could be used for component 68. For example, a scissor jack-like mechanism or inclined planes could be used to move the sections to its expanded position. In addition, multiple sections can be used that expand in multiple directions.

In another embodiment, a rod component similar to that shown in FIGS. 2–6 is inserted between sections of component 68 in its expanded expansion. The implanted rod may be held in position within component 68 by adding a taper to the interior surfaces of sections 68a and 68b.

Upper outer sleeve 32 which contains textured surface area 34 in FIG. 2 can be adapted to further enhance bone ingrowth in devices according to the present invention. FIGS. 9A–C demonstrate several alternative embodiments which may be used to further promote this growth. Referring now to FIG. 9A, upper outer sleeve 34 contains a plurality of wells 80 along its outer surface which replaces the textured surface. Wells 80 are filled with collagen sponges 82 which have been soaked with Bone Morphogenetic Protein (BMP). Sponges 82 are inserted into wells 80 prior to insertion of device 30 into femur 20. In FIG. 9C, sleeve 34 contains a plurality of channels 84 which extend along the length of sleeve 34. In this embodiment, BMP could be injected into channels 84 after insertion of device 30, or BMP soaked collagen sponges 82 may be forced into channels 84.

Another alternative embodiment of an arthroplasty device according to the present invention is shown in FIGS. 10A–C. A femoral rod component 90 having an outwardly extending stem 92 and a collar stop 94 in installed through a sleeve 96 having a textured area 98 for promoting bone ingrowth. The interior of sleeve 96 contains of pair of grooves 100 which correspond to a pair of wings 102 extending from the outer surface of component 90 such that the interaction of wings 102 and grooves 100 allow small amounts of motion between rod component 90 and sleeve 96 to decrease the shear stress on textured area 98 where bone ingrowth occurs. Shear stress can cause motion between the device and the patient's bone, decreasing the chance of bone ingrowth. Devices using anti-rotation features, such as shown in FIG. 10C and FIG. 7, will have rods with varying degrees of version, including antiversion and retroversion.

Figure 11A:
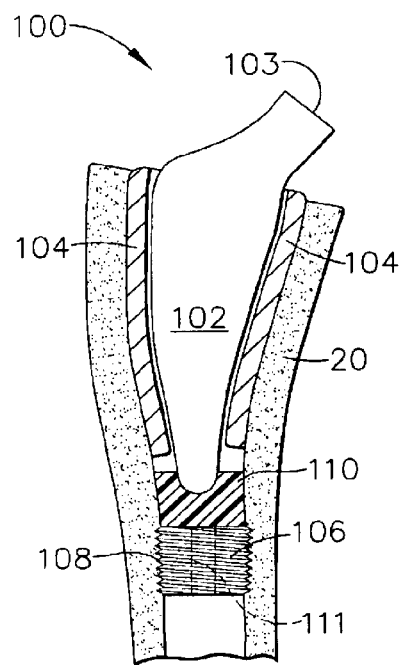
FIG. 11A is a lateral view, partly in cross section, of another embodiment of the present invention.

FIGS. 11A–E show an alternative embodiment of the device according to the present invention which uses resorbable components to temporarily decrease or remove the stress on the bone ingrowth surfaces of the device. Referring now to FIG. 11A, an arthroplasty device 100 similar to the device of FIG. 10A–C is shown, having a femoral rod component 102 with a outwardly extending stem 103, a positioning sleeve 104 having a textured area (not shown) for promoting bone growth, and a solid disc 106 having an threaded outer surface 108. Disc 106 is initially positioned within a femur 20. Disc 106 has been installed into position within femur 20, after its interior has been threaded in the appropriate area by using a tool similar to that shown in FIG. 5A. Alternatively, outer surface 10B may contain self-tapping threads. Resorbable material 110 is threaded into femur 20, contacting disc 106, and then rod component 102 is introduced into sleeve 104. Note that component 102 is supported by resorbable material 110 and not sleeve 104. Preferably, device 100 contains the anti-rotation features shown in FIG. 10C. Additionally, anti-rotation features can also be added between disc 106, resorbable material 110 and the end of rod component 102 for additional stability. Suitable resorbable materials include a high molecular weight poly-L-lactic acid (PLLA) polymers, calcium hydroxyapatite, tricalcium phosphate. Other potentially useful resorbable materials include polydiaoxanone (PDS), oxidized regenerated cellulose and various forms of collagen.

Figure 11B:
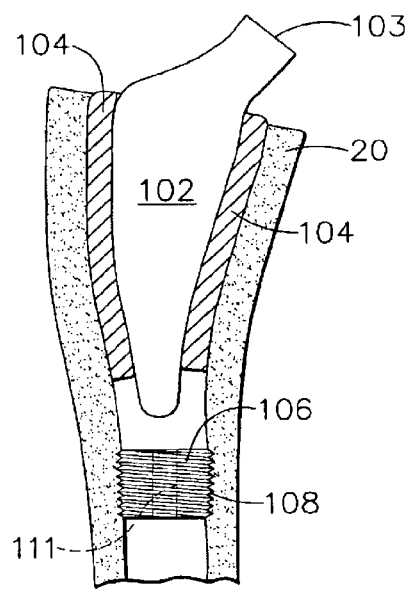
FIG. 11B is a lateral view, partly in cross section, of the device of FIG. 11A after a period of time.

In this relationship, resorbable material 110 temporarily decreases or removes the stress on the bone ingrowth surfaces of sleeve 104. The forces on device 100 are transferred from resorbable material 110 to the ingrowth surfaces of sleeve 104 as resorbable material 110 disappears. Disc 106 may also contain a through hole 111 to aid in the drainage of resorbable material 110. This resorption process generally takes months. Bone will grow into the ingrowth area of sleeve 104 while device 100 is supported by resorbable material 108. Eventual transfer of the forces to the ingrowth area of device 100 is important to prevent bone resorption that occurs with stress shielding. Resorbable material 110 may also temporarily eliminate movement through device 100. Eliminating movement across device 100 decreases forces on the bone ingrowth surfaces. Motion through device 100 is permitted once resorbable materials 110 has dissolved, as rod component 102 now contacts sleeve 104, as can be seen in FIG. 11B.

Figure 11C:
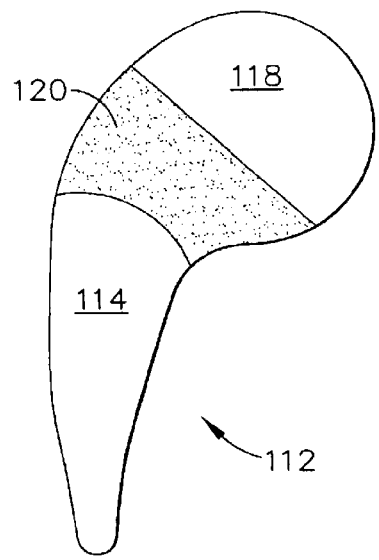
FIG. 11C is a lateral view of another embodiment of the present invention.
Figure 11D:
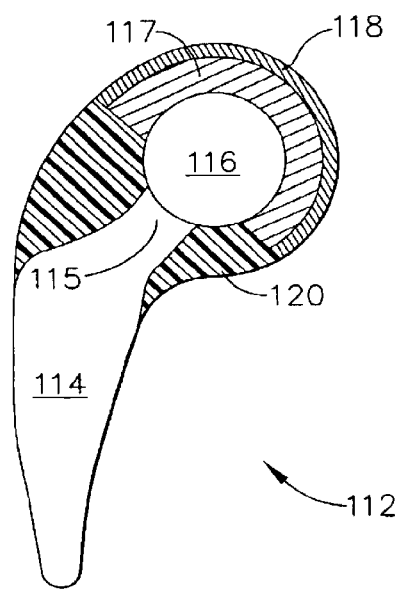
FIG. 11D is a cross-sectional view of the device of FIG. 11C.

A prosthetic hip device according to the present invention is shown in FIGS. 11C–D. Hip device 112 includes a femoral rod component 114 having an outwardly extending stem 115, a head 116 mounted on stem 115, an inner acetabular component 117, and an outer acetabular component 118. A resorbable component 120 is located between component 118 and rod component 114 to restrict motion between the acetabular and femoral components of device 112 until resorbable component 120 disappears, allowing time for bone ingrowth to firmly take hold.

Figure 11E:
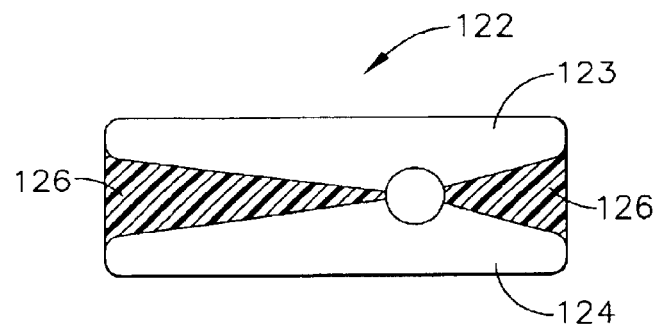
FIG. 11E is a lateral view of another embodiment of the present invention.

FIG. 11E shows prosthetic disc replacement device 122 according to the present invention. Device 122 includes an upper plate 123 and a lower plate 124 connected by a pivot 125. Resorbable material 126 is placed between plates 123 and 124 before insertion of device 122 into a position between vertebrae of the spine.

Figure 12A:
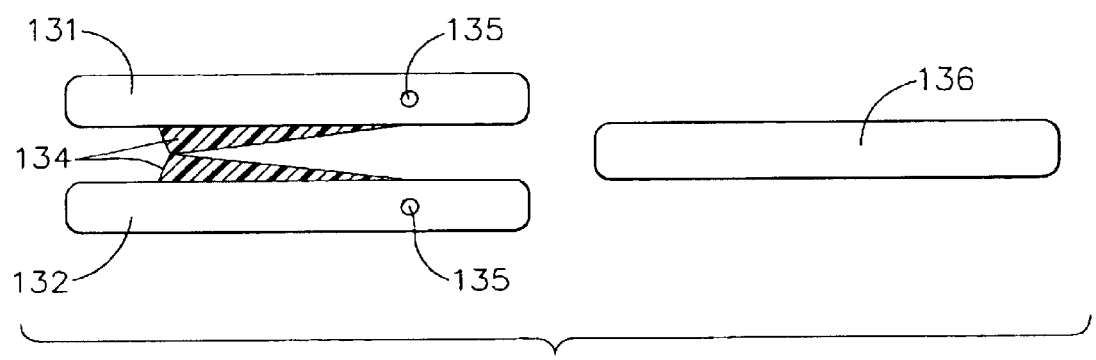
FIG. 12A is a lateral view of an alternative device according to the present invention for use in prosthetic disc replacement shown in the unassembled position.
Figure 12B:
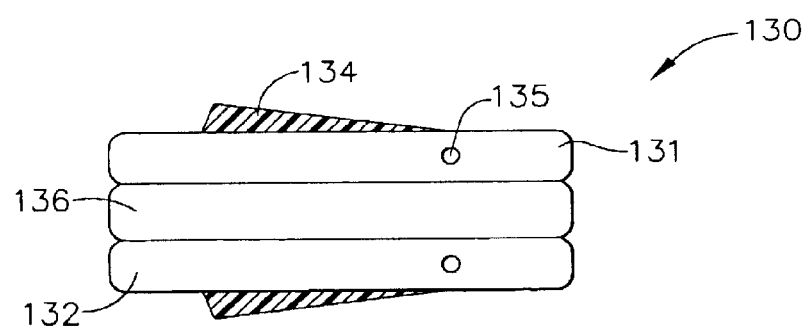
FIG. 12B is a lateral view of the device of FIG. 12A in the assembled position.

FIGS. 12A–B show an alternative embodiment of a prosthetic disc replacement device 130. Device 130 contains an upper plate 131 and a lower plate 132. Each plate contains a keel-like ingrowth extension component 134 attached for rotation through plates 131, 132 at a pivot 135. An activation device 136 consisting of a flat plate is also shown. To install device 130, the device is placed between vertebrae in the spine of a patient. Activation device 136 is pushed between plates 131 and 132 to force extensions 134 away from plates 131, 132 to affix device 130 in its proper location between the vertebrae. Extensions 134 are exposed to the cancellous bone of the vertebrae, immobilize device 130 and help prevent its extrusion.

Figure 13:
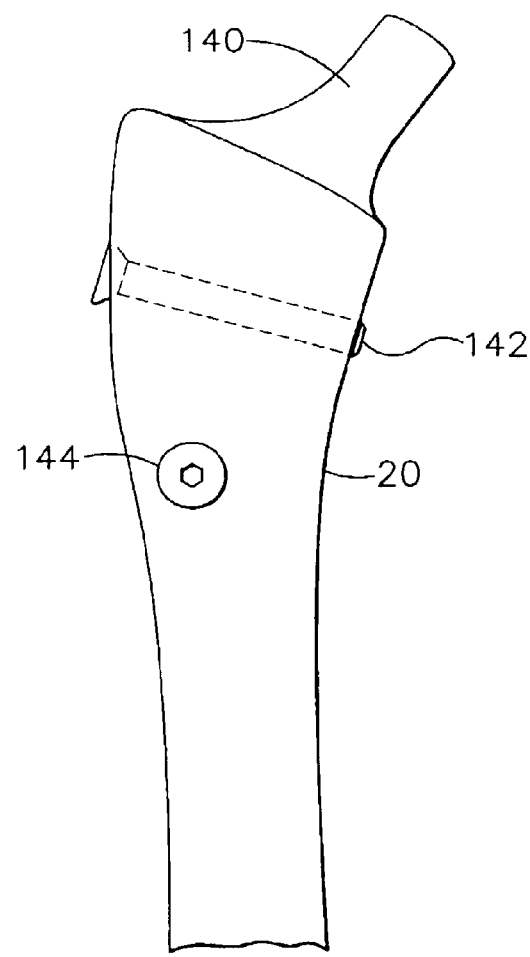
FIG. 13 is a lateral view of a femoral component according to the present invention.

FIG. 13 shows another embodiment of a method for restricting motion of the prosthesis relative to the bone when using an arthroplasty device. Referring now to FIG. 13, there is shown a femoral component 140 positioned within femur 20. Component 140 is held firmly in place by a first screw 142 which is affixed crosswise through component 140 and femur 20. A second screw 144 is affixed through component 140 and femur 20 in a direction oriented approximately 90° to first screw 142. A guide is preferably removably attached to femur 20 or component 140 to help direct a drill bit through femur 20 and to thread screws 142 and 144 through the structure. Use of screws 142 and 144 assist in minimizing motion of component 140 with respect to femur 20, allowing bone ingrowth between component 140 and femur 20.

Figure 14:
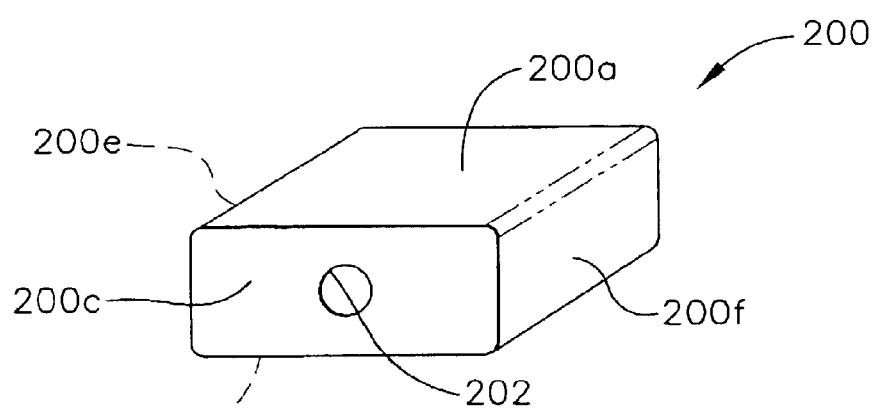
FIG. 14 is a perspective view of another embodiment of the present invention.

FIG. 14 shows a device which promotes bone ingrowth in a spinal fusion procedure. Implant 200 consists of a box-like structure having top and bottom surfaces 200a, 200b, front and rear surfaces 200c, 200d, and side surfaces 200e, 200f. In this embodiment, surfaces 200a and 200b are essentially parallel, 200c and 200d are essentially parallel, and 200e and 200f are essentially parallel; however, implant 200 can consist of any shape which will fit between adjacent vertebrae. Surface 200c contains an aperture 202 which allows access to the interior of implant 200. Aperture 202 allows for the injection of a bone growth promoting substance into implant 200. Possible substances include Platelet Rich Plasma (PRP), bone morphogenetic protein (BMP), or concentrated leukocytes. Other substances which are available are discussed in my co-pending patent application Ser. No. 09/897,000, which application is incorporated by reference herein. Although implant 200 is preferably manufactured from bone, it could also be constructed from other compatible materials such as metal or polymers. Alternatively, the metal or polymer devices could be filled with bone.

Figure 15A:
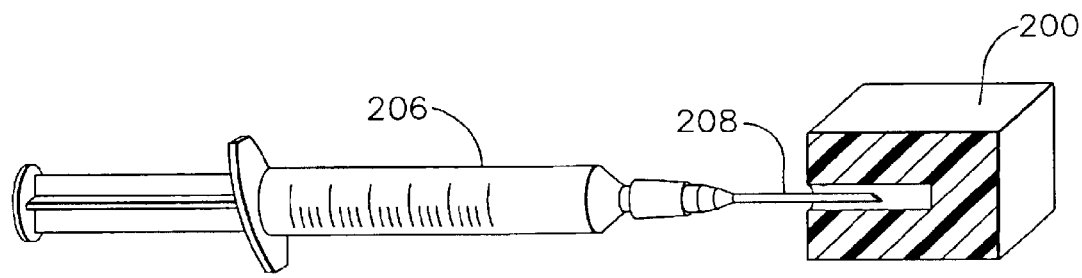
FIG. 15A is a perspective view of the device of FIG. 14 with a portion of the device removed and a syringe shown for injecting a bone growth promoting substance into the device.
Figure 15B:
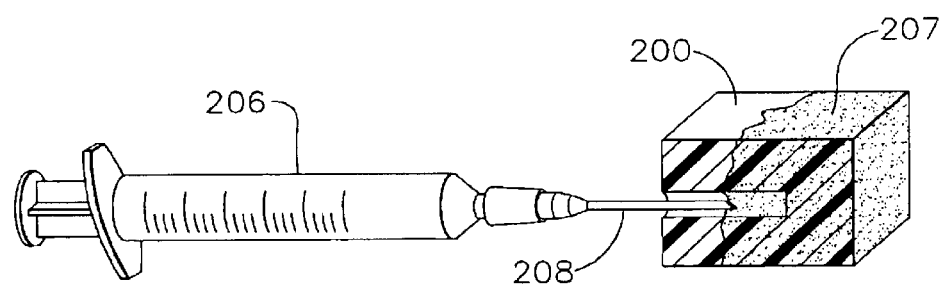
FIG. 15B is a perspective view of FIG. 15A showing the device of FIG. 14 partially filled.
Figure 16A:
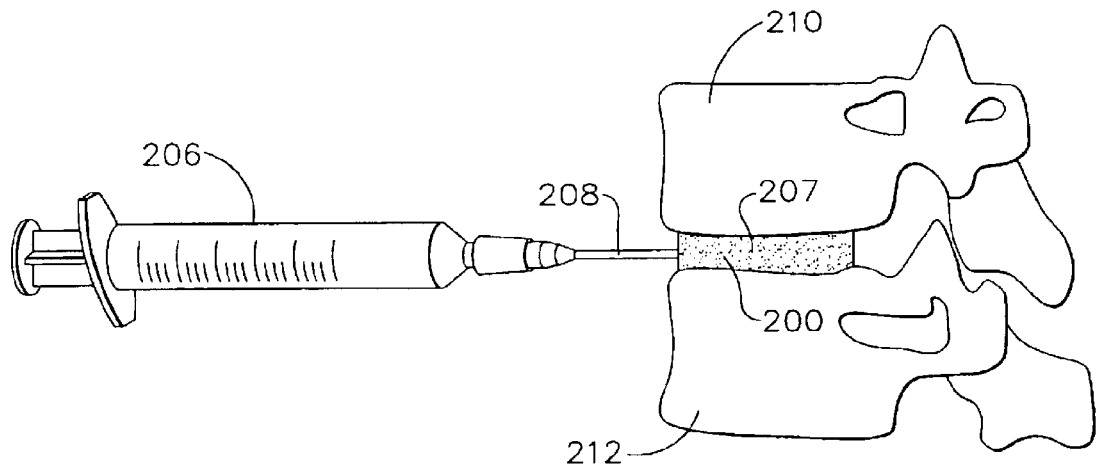
FIG. 16A is a lateral view of a section of the spine showing the device of FIG. 14 installed in position between the vertebrae.

FIGS. 15A–B show how implant 200 can be filled with an appropriate bone growth promoting substance. A syringe 206 filled with a suitable substance 207 is positioned with its needle 208 inserted through aperture 202. As syringe 206 is operated, substance 207 fills implant 200 with the bone growth promoting fluid, as can be seen clearly in FIG. 15B. FIG. 16A shows implant 200 in position between adjacent vertebrae 210, 212 while syringe 206 injects growth substance 207 into the implant.

Figure 16B:
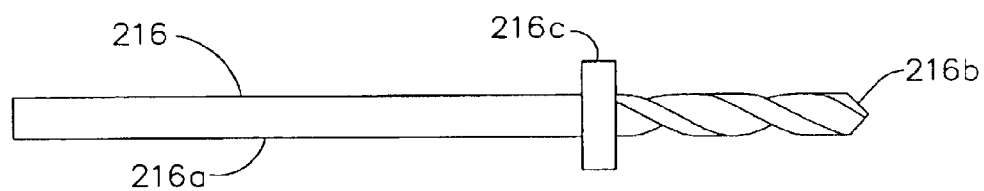
FIG. 16B is a lateral view of a drill bit which may be used to create a hole in the device of FIG. 14.
Figure 17:
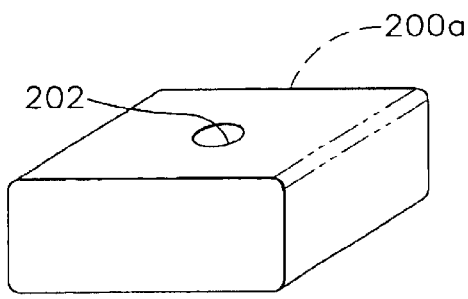
FIG. 17 is a perspective view of an alternative embodiment of the device of FIG. 14.

A drill bit 216 is shown in FIG. 16B which may be used to create aperture 202 in implant 200. Bit 216 contains a smooth cylindrical section 216a, a fluted end 216b having a point for drilling, and a collar stop 216c. Drill bit 216 is particularly suited for drilling aperture 202 into implant 200, as collar stop 216c acts to prevent bit 216 from traveling too far into implant 200, possibly damaging the device. Drill bit 216 may be helpful when drilling aperture 202 into a device such as implant 200a, which has a different shaped structure, as can be seen in FIG. 17. Aperture 202 can be aligned in any suitable direction within the device. While aperture 202 can be drilled into implant 200 before inserting the device into position in the spine, it may be advantageous to drill aperture 202 into implant 200 after it is positioned between vertebrae 210, 212. This would avoid weakening of implant 200, as the device is under compressive forces when in position. Alternatively, implant 200 could be manufactured with aperture 202 in place in the device.

Figure 18A:
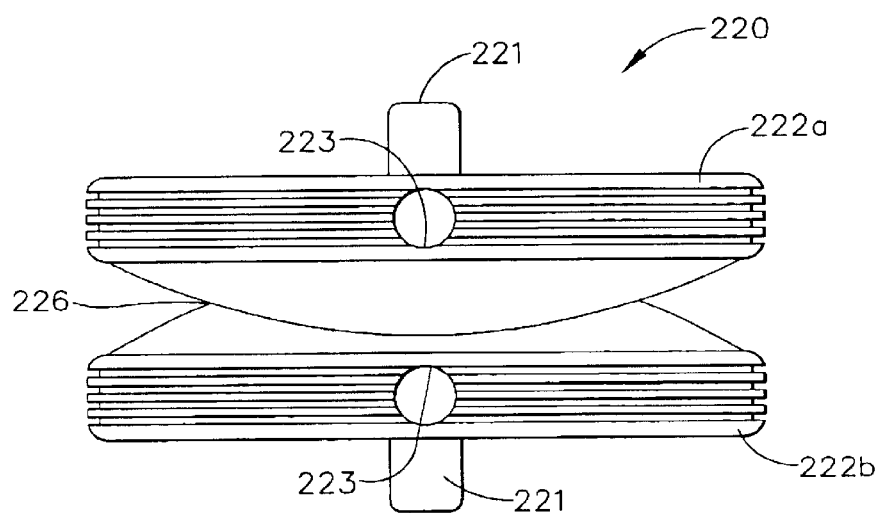
FIG. 18A is an end view of an alternative artificial disc replacement device for use in the present invention.
Figure 18B:
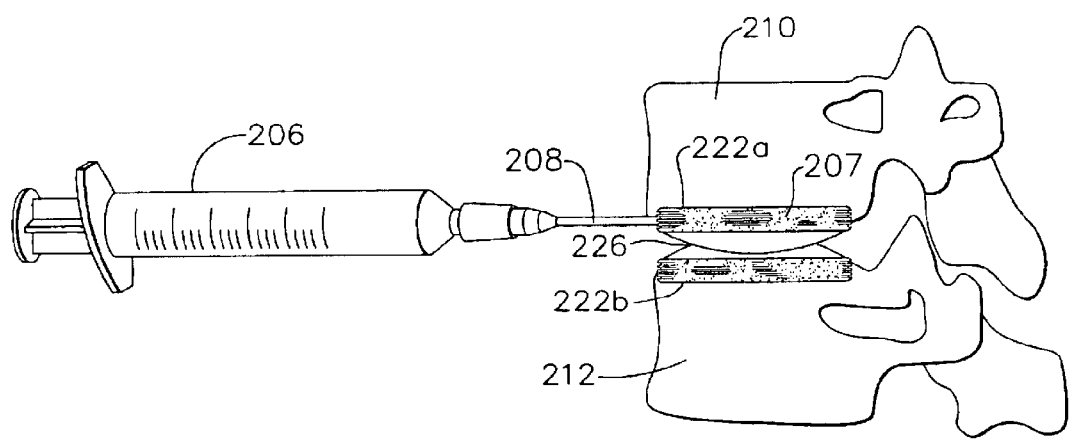
FIG. 18B is a sectional view of the device of FIG. 18A positioned between vertebrae of the spine.

Bone growth promoting substances can be used in many other arthroplasty devices. FIGS. 18A–B show its use in connection with an artificial disc replacement (ADR) procedure. An ADR device 220 similar to the device of FIGS. 12A–B contains a pair of extensions 221 for fixing device 220 in the spine and a pair of end plates 222a, 222b each having an aperture 223. End plates 222a, 222b are separated by an activating structure 226. End plates 222a, 222b may contain a series of channels which are connected to apertures 223. When device 220 has been positioned in place between vertebrae 210, 212, syringe 206 can be located with needle 208 inserted into apertures 223 of end plates 222a, 222b to input growth substance 207 into device 220 to promote bone ingrowth between the device and the vertebrae.

Figure 19:
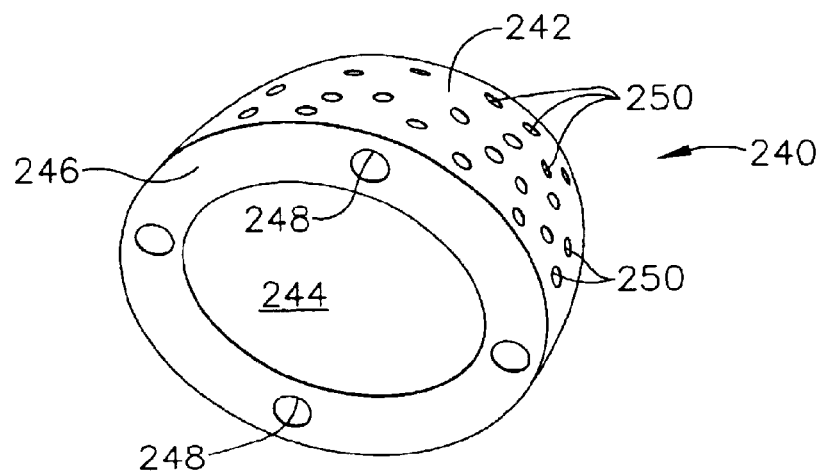
FIG. 19 is a perspective view of an acetabular component for use in an embodiment of the present invention.
Figure 20:
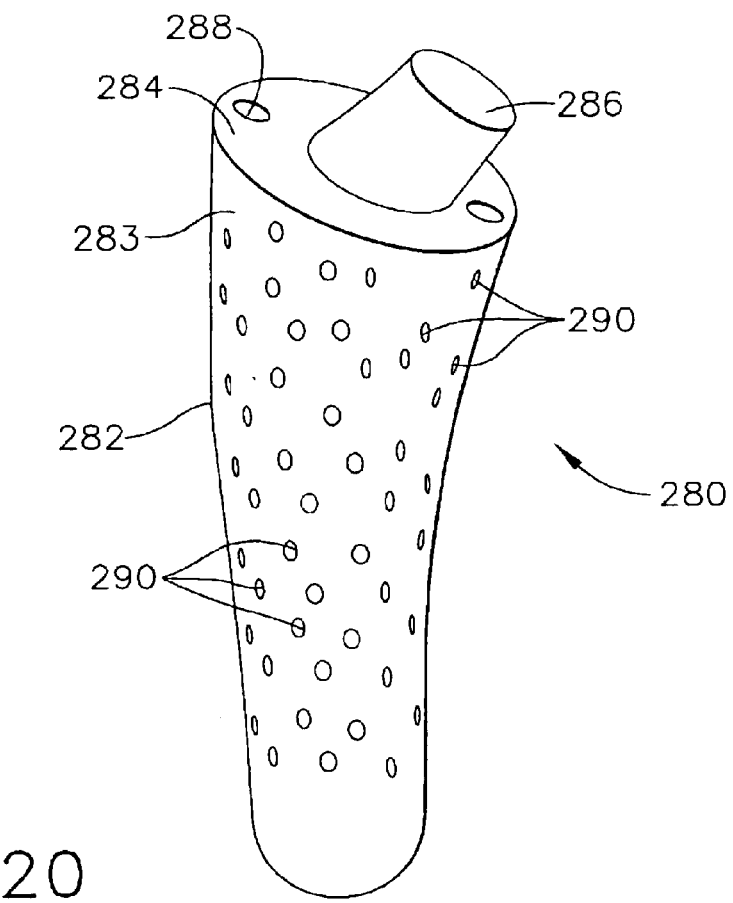
FIG. 20 is a perspective view of a femoral component for use in an embodiment of the present invention.
Figure 21:
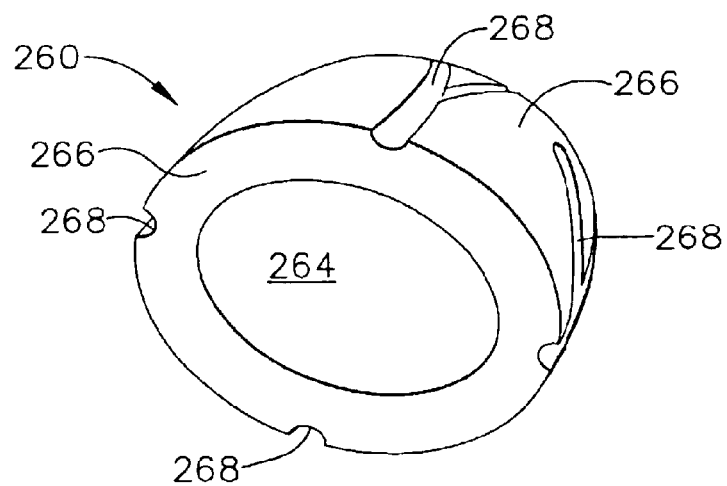
FIG. 21 is a perspective view of an alternative acetabular component similar to the device of FIG. 19.

FIGS. 19 to 22A–B depict different arthroplasty devices which can be used in conjunction with bone growth promoting substances to maximize bone ingrowth between the body and the implants. An acetabular component for use in hip replacement is shown in FIG. 19. Component 240 is a cup-shaped device having a spherical outer surface 242 and a hollow curved inner surface 244. A front surface 246 contains a plurality of apertures 248. Apertures 248 are connected to a series of channels which are connected to a series of outlets 250 which are scattered along outer surface 242 of device 240. When component 240 is placed in position during hip replacement surgery, bone growth substance 207 can be injected into apertures 248 such that the substance can travel through the channels to outlets 250, where it can contact the hip bone to promote bone ingrowth between device 240 and the bone. An alternative embodiment to implant device 240 is shown in FIG. 21. This acetabular component 260 has a spherical outer surface 262, a hollow curved inner surface 264 and a flat front surface 266. Along the periphery of surface 266 a series of grooves 268 are channeled into outer surface 262. Grooves 268 may be parallel channels along outer surface 262, or they may spiral around outer surface 262. When component 260 is positioned in the bone during hip surgery, growth substance 207 may be injected into grooves 268 such that the fluid can flow between component 260 and the bone to promote bone ingrowth.

Figure 22A:
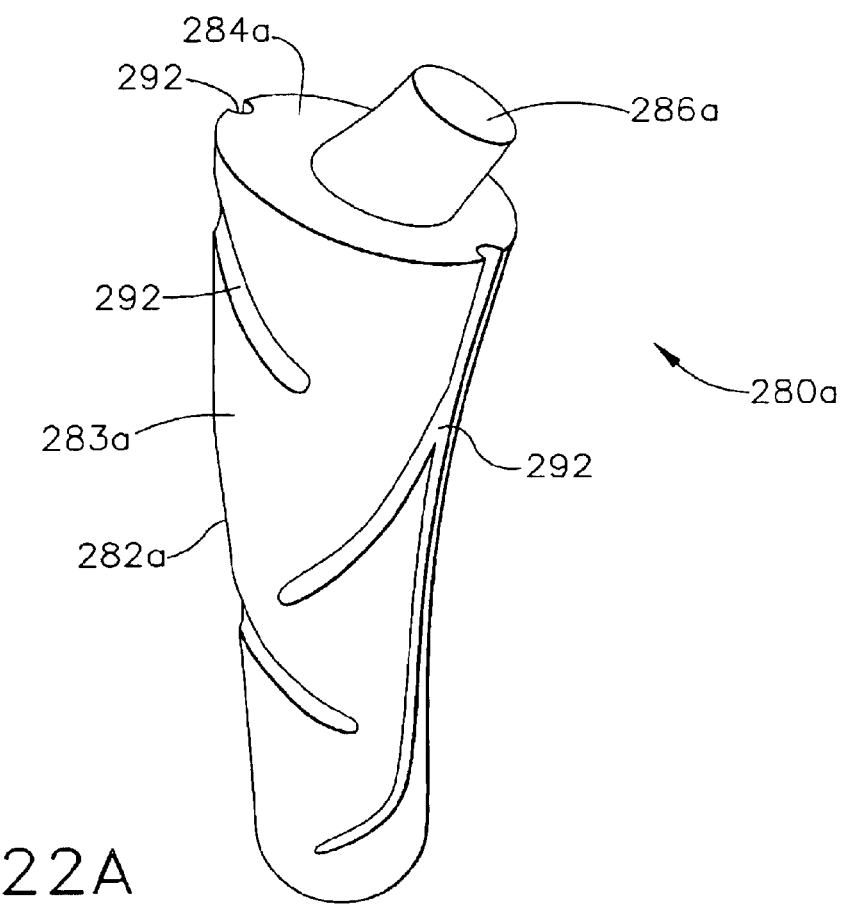
FIG. 22A is a perspective view of an alternative femoral component similar to the device of FIG. 20.
Figure 22B:
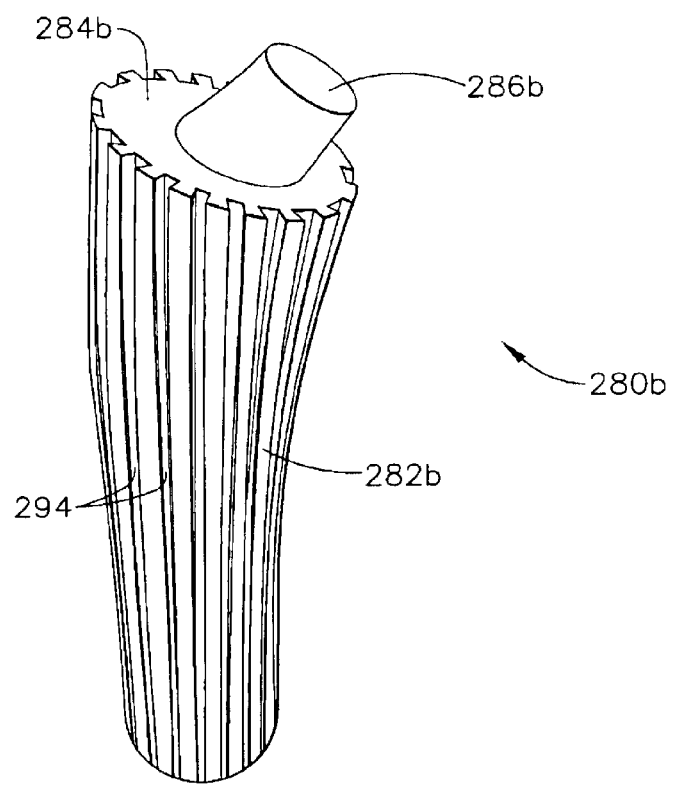
FIG. 22B is a perspective view of another alternative femoral component similar to the devices of FIG. 20 and FIG. 22A.

Examples of the present invention for use with femoral components are shown in FIGS. 20 and 22A–B. Referring now to FIG. 20, a femoral component 280 is shown having a body 282 having an outer surface 283, a flat top surface 284, and an outwardly extending stem 286. A plurality of apertures 288 are located on flat surface 284.

A series of channels within body 282 are connected to apertures 288 at one end, while the other ends are connected to a series of outlets 290 located on outer surface 283. When component 280 is implanted in position within a femur, bone growth substance 207 is injected into apertures 288 such that it will travel through body 282 and exit through outlets 290 between component 280 and the bone to promote bone ingrowth. Alternative versions of this device are shown in FIGS. 22A–B. In FIG. 22A, femoral component 280a contains a body 282a having an outer surface 283a, a flat top surface 284a, and an outwardly extending stem 286a. Along the periphery of surface 284a, a plurality of grooves 292 are channeled into the outer surface 283a. Grooves 292 may be straight along outer surface 283a, or they can spiral around component 280a. When component 280a is fixed in place within a femur, growth substance 207 can be injected into grooves 292 such that the fluid can flow between the implant 280a and the bone to promote bone ingrowth. FIG. 22B shows a similar device 280b, except that grooves 294 are equally spaced around the periphery of upper surface 284b and are oriented in a parallel fashion along outer surface 283b.

The principles of the present invention taught in FIGS. 19–22B can be applied to other prosthetic devices such as knee replacements, shoulder replacement, and spinal fusion cages.

Figure 23A:
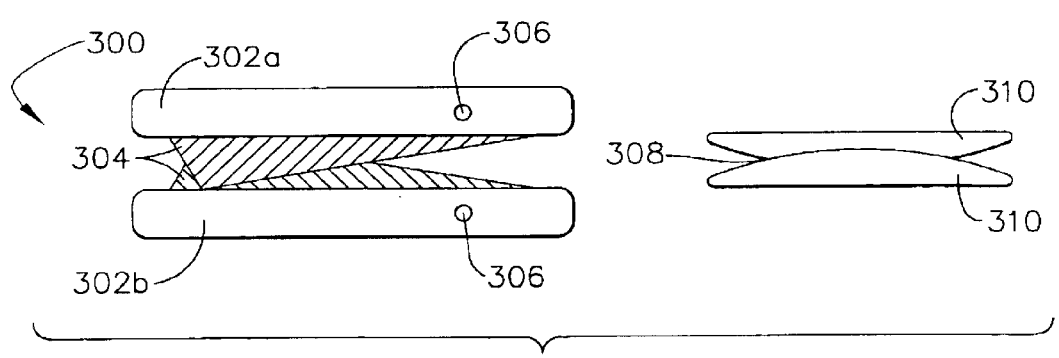
FIG. 23A is a lateral view of an alternative embodiment of the device of FIG. 12A.
Figure 23B:
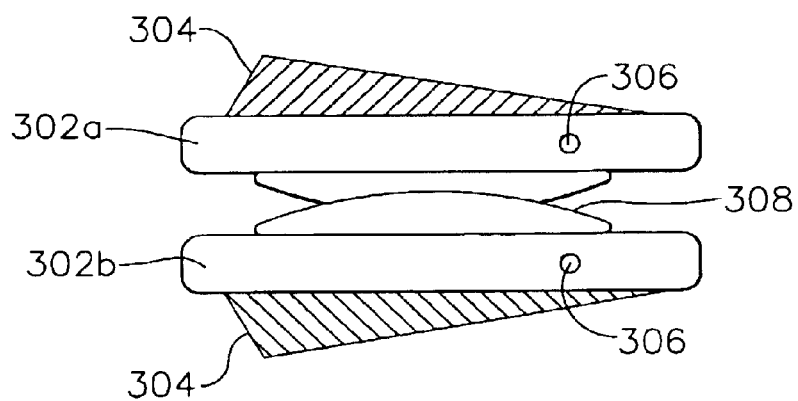
FIG. 23B is a lateral view of the device of FIG. 23A shown in the deployed position.

FIGS. 23A–D teaches several alternative embodiments of the present invention for use in spinal procedures similar to those taught in FIGS. 12A–B and FIGS. 18A–B. Referring now to FIG. 23A, there is shown a spinal device generally indicated at 300 having a pair of end plates 302a, 302b. Each end plate contains a keel-like fixation component 304 which is fixed for rotation about a pivot 306 through the interior area of the end plate. Component 304 are offset from each other with respect to device 300 such that component 304 rest side by side between end plates 302a, 302b when device 300 is in the unactivated position. This orientation allows for larger fixation components to be used in device 300 for better fixation in position between vertebrae. An activating component 308 is shown alongside device 300. Component 308 consists of a pair of spherical pusher plates 310. In operation, activating component 308 is forced between end plates 302a, 302b, causing fixation components 304 to rotate about pivot points 306 outwardly through end plates 302a, 302b, to extend from device 300 and holding the device firmly between vertebrae of the spine, as is shown in FIG. 23B.

Figure 23C:
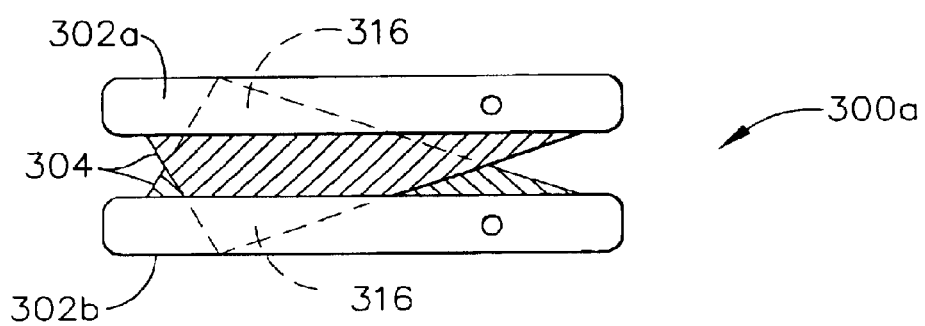
FIG. 23C is a lateral view of an alternative embodiment of the device shown in FIG. 23A.
Figure 23D:
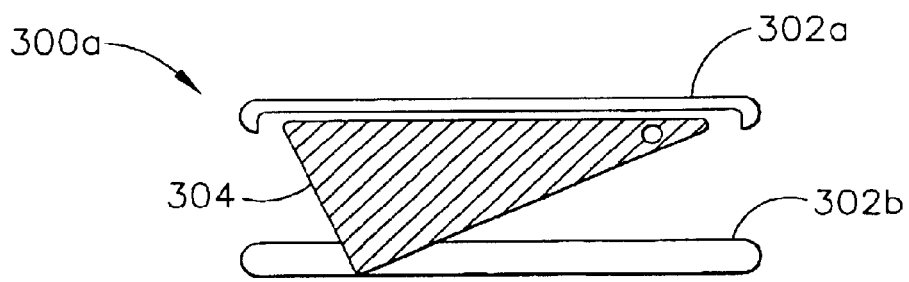
FIG. 23D is a sectional view of the device of FIG. 23C.

FIGS. 23C–D show spinal device 300a in which slots 316 are incorporated into end plates 302a, 302b such that fixation components 304 rest within slots 316 when device 300a is in the unactivated state. Slots 316, which may be shaped such that the end of each fixation component 304 just fits within said slot, or may extend along a longer portion of each end plate, to allow for the use of a larger fixation component with device 300a, improving the holding power of spinal device 300a when positioned between vertebrae.

Figure 24C:
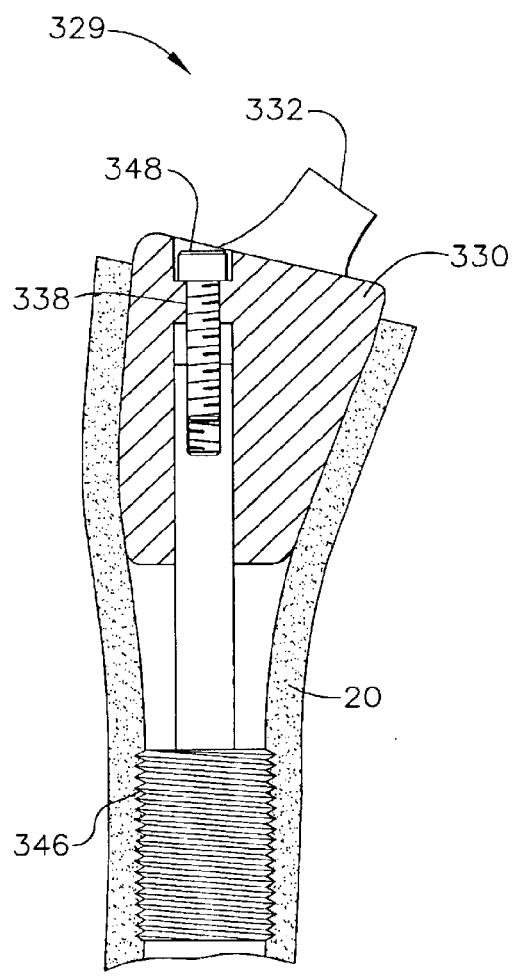
FIG. 24C is a cross-sectional view of the device of FIG. 24A installed in the femur.

FIGS. 24A–D show an alternative embodiment for an arthroplasty device according to the present invention for use in hip surgery. Referring now to FIGS. 24A–C, there is shown a device 329 having a femoral component 330 with a outwardly extending stem 332, and a hollow passageway 334 extending through the central area of component 330. Passageway 334 is square shaped in this embodiment, but it may be shaped in any configuration in which a component inserted into said passageway cannot rotate, such as an ellipse, a triangle, pentagon, or hexagon. Component 330 also contains a recess 336 on its upper surface. Passageway 334 and recess 336 are connected by a channel 338. An attachment component 340 contains an upper section 342 having a square shape with a threaded aperture 344 at its upper end and a lower threaded cylindrical section 346. A screw 348 is also provided with the device.

To install femoral component 330 into a femur in a hip replacement procedure, the inner surface of femur 20 is threaded at the proper depth using a tool similar to that shown in FIG. 5A. Attachment component 340 is installed within femur 20 by threading section 346 into the femur. Component 330 is then located upon upper section 342 of attachment component 340 by matching the shape of section 342 with recess 334 in the proper orientation. Screw 348 is then inserted into recess 336 of component 330 through channel 338 and threaded into aperture 344 to hold the device in its proper position within femur 20. This procedure "pulls" the device into the femur, helping to prevent fracturing the bone. A torque wrench may be used to adequately tighten screw 348 to its proper tightness to prevent splitting femur 20. Attachment component 342 may be composed of a polymer such as carbon fiber, or alternatively may be composed of a resorbable material. Device 329 minimizes motion between the implant and bone, as the matched shape connection between passageway 334 and upper section 342 of attachment component 340 allows for virtually no movement.

Figure 24D:
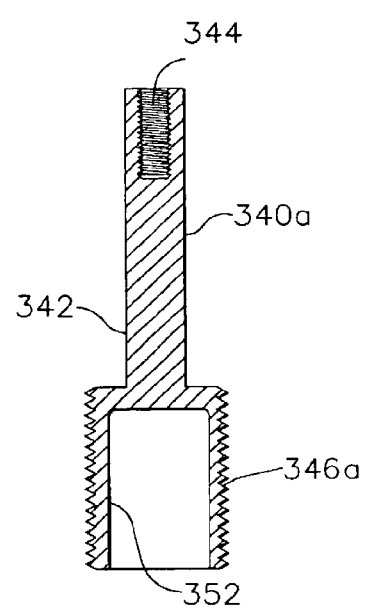
FIG. 24D is a cross-sectional view of an alternative embodiment the threaded component shown in FIG. 24A.

An alternative attachment component 340a for component 340 is shown in FIG. 24D. Component 340a contains a similar upper section 342 containing a threaded aperture 344; however, lower cylindrical threaded section 346a contains a hollow internal section 352. Hollow section 352 gives threaded section 346a more flexibility than a solid component. Hollow threaded components and polymer threaded components are less likely to cause thigh pain from excessive stress transfer to the femur at the level of the threaded component. Furthermore, resorbable components, in particular, are less likely to cause stress shielding of the proximal femur.

Figure 25A:
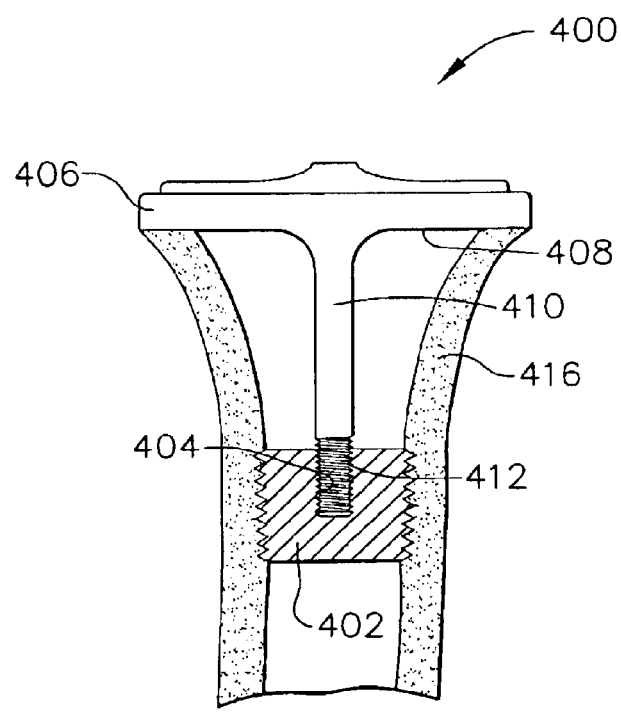
FIG. 25A is a cross-sectional view of a device according to the present invention installed in the tibia.
Figure 25B:
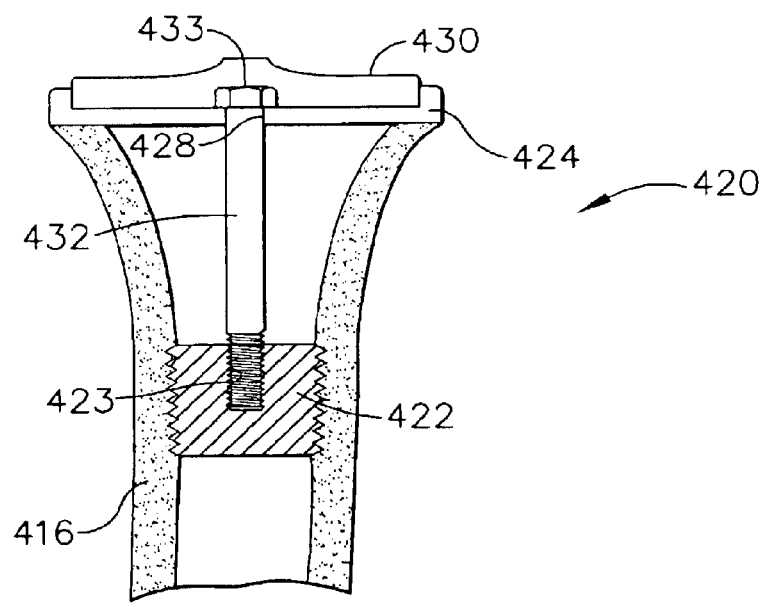
FIG. 25B is a cross-sectional view of an alternative embodiment of the device of FIG. 25A.

FIGS. 25A–B show an embodiment of the present invention for use in a prosthetic knee device. Device 400 includes a cylindrical component 402 having a threaded outer surface and a recess 404 having a threaded inner surface. An articulating component 406 includes a planar section 408 having an extension 410 with a treaded end 412.

To install device 400, the internal surface of tibia 416 is threaded internally using a device similar to that shown in FIG. 5A at the desired depth. Component 402 is then threadably engaged within tibia 416. Articulating component 406 is then threadably affixed to component 402 by threading end 412 of extension 410 into recess 404 until surface 408 contacts tibia 416.

Referring now to FIG. 25B, prosthetic device 420 includes a cylindrical component 422 having a threaded outer surface and an aperature 423 having a threaded inner surface, and an upper component 424 having a planar surface 426 and an aperture 428 in the central region. The upper surface of component 424 is sized such that a cover 430 may be snapped into position on the upper surface. Cover 430 may be constructed of polyethylene. A bolt 432 having a head 433 is also included with device 420.

To install device 420, the internal surface of tibia 416 is threaded internally using a device similar to that shown in FIG. 5A at the desired depth. Upper component 424 is placed on the upper surface of tibia 416 and bolt 432 is placed through aperture 428 and is threaded into aperture 423 of component 422 until head 433 contacts the upper surface of component 424. Cover 430 is then snapped into position on component 424.

In FIGS. 25A–B, components 402 and 422 may be composed of metal or a polymer, or could also be made from a resorbable material. Components 406 and 429 may be constructed from titanium or chrome cobalt.

Figure 26:
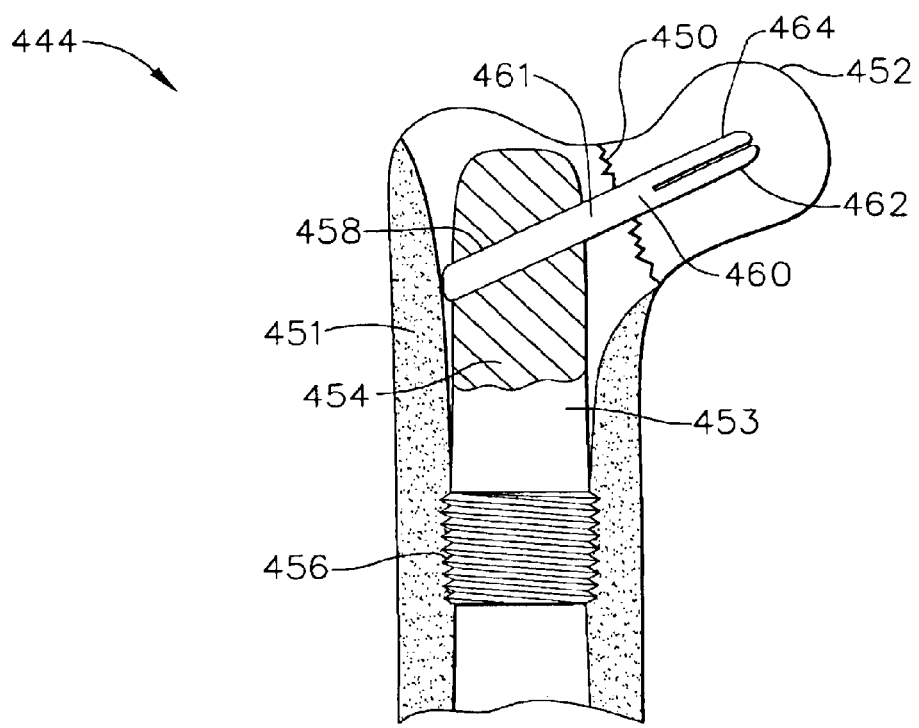
FIG. 26 is a cross-sectional view of a device according to the present invention installed in the proximal femur.

FIG. 26 shows a device 444 embodying the present invention for use in treating the hip socket. In this embodiment, a fracture 450 of a femur 451 is shown at the base of the femoral head 452. Device 444 includes a femoral repair component 453 consisting of a cylindrical member 454 having a threaded end section 456. Component 453 also contains an aperture 458 which is oriented angularly toward femoral head 452. Aperture 458 may be threaded internally. A second component 460 of device 444 consisting of a connecting rod 461 having a threaded end 462 is connected to femoral head 452 by a threaded aperture 464 within femoral head 452.

To install device 444 for repair of the fractured femur, threaded end section 456 is located within femur 451 using the techniques previously discussed. The correct angular position of component 460 relative to component 453 and femoral head 452 is determined, and threaded end 462 is affixed within femoral head 452. Rod 461 is sized such that the end can be inserted into aperture 458 of component 453 using a small amount of force to overcome the friction fit between the components. Rod 461 is then inserted into aperture 458 until femoral head 452 is positioned against femur 451. The interaction between rod 461 and component 453 acts to hold head 452 in the correct position to heal.

Figure 27A:
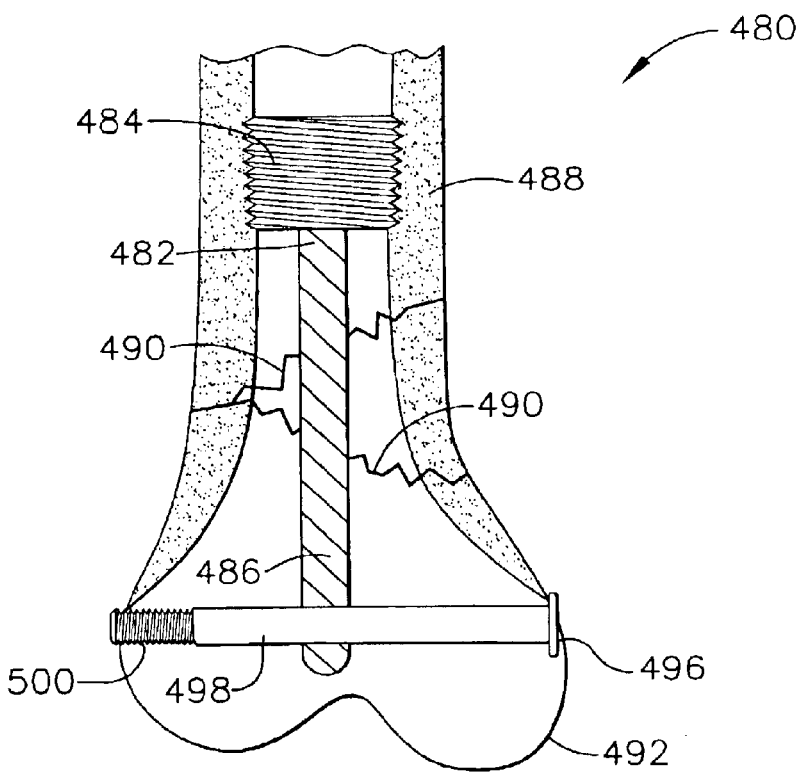
FIG. 27A is a cross-sectional view of a device according to the present invention installed in the distal femur.
Figure 27B:
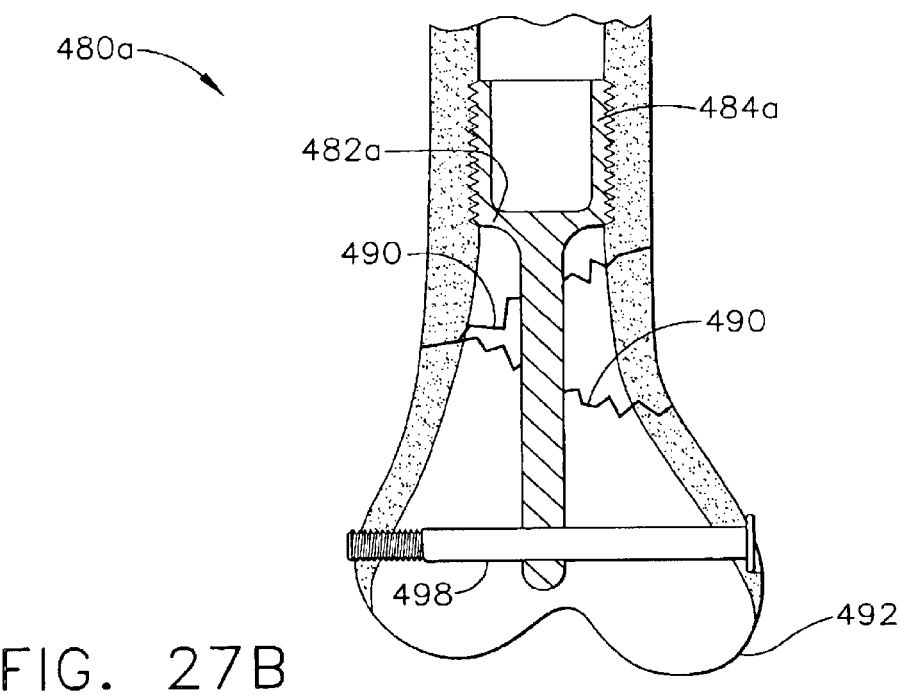
FIG. 27B is a cross-sectional view of an alternative embodiment of the device of FIG. 27A installed in the distal femur.

FIGS. 27A–B show an embodiment of the present invention for use in repairing a fracture of the distal end of the femur. Repair device 480 includes a component 482 having a solid first section 484 with a threaded outer surface and a narrower cylindrical second section 486. To install repair device 480, the internal surface of femur 488 is threaded at a section on the opposite side of fracture 490 from distal end 492 of femur 488 using a device similar to that shown in FIG. 5A. Threaded section 484 of component 482 is affixed within femur 488 such that section 486 is spaced apart from distal end 492 of femur 488 when the two sections of femur 488 are held together tightly along fracture 490. A hole 496 is then drilled across the distal end 492 of femur 488, passing through section 486 of component 482. A screw 498 is then placed into hole 496, passing through section 486 of component 482 and is threaded into femur 488 as shown at 500. This device holds the sections of femur 488 tightly together to aid in the healing process. Threaded section 484 can be made from a resorbable material, non-resorbable polymers, metal, or a combination of materials. For example, section 484 could be made with a metal core surrounded by a resorbable component.

The device 480a of FIG. 27B is similar to device 480 shown in FIG. 27A except for the design of component 482. Component 482a is constructed like the component shown in FIG. 24D in that first section 484a is hollow with a threaded outer surface. As discussed previously, the hollow section allows more flexibility than a solid component. The installation of device 480a follows the same methods of that taught for device 480.

Figure 28A:
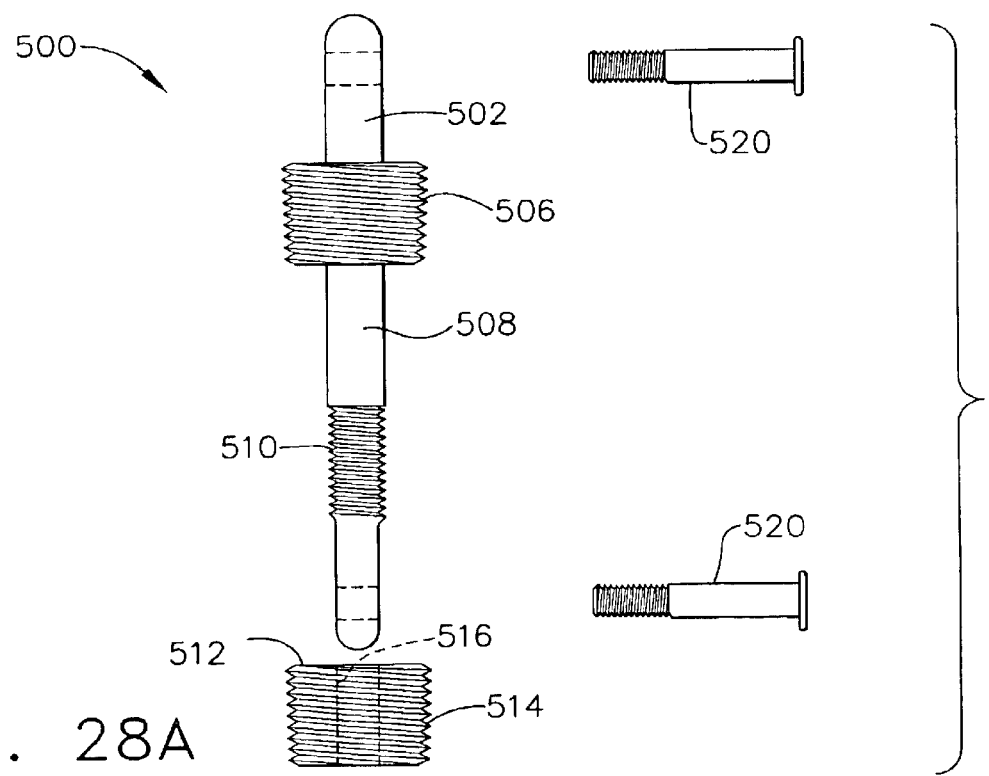
FIG. 28A is an exploded view of a device according to the present invention for use in a long bone.
Figure 28B:
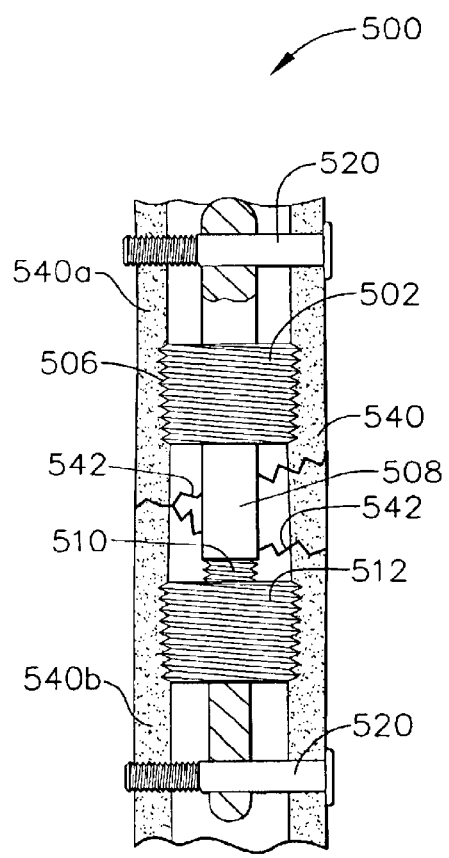
FIG. 28B is a cross-sectional view of the device of FIG. 28A invention installed in a long bone.
Figure 28C:
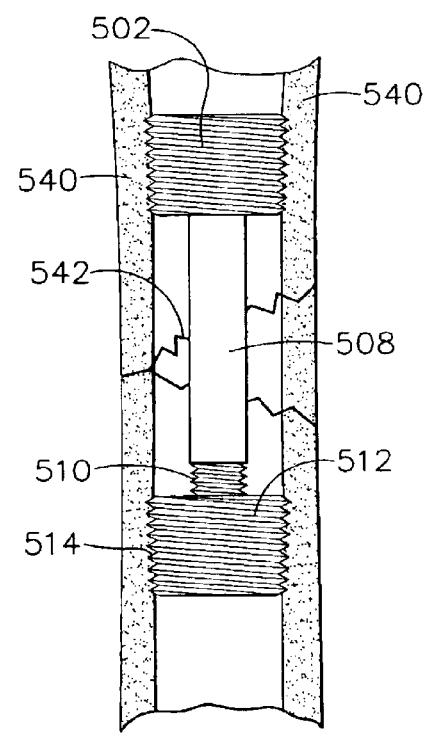
FIG. 28C is a cross-sectional view of an alternative embodiment of the device of FIG. 28A.

FIGS. 28A–C show a fixation device 500 for use in long bones. Referring now to FIG. 28A, a first component 502 contains a solid cylindrical portion 504 having an outer threaded surface 506, and a cylindrical portion 508 having a lesser diameter than portion 504 and containing a threaded portion 510 located along its length. A second component 512 comprises a cylindrical disc having a threaded outer surface 514 and a central aperture 516 which is threaded. In addition, a pair of screws 520 are provided.

Fixation device 500 is shown on its installed position in FIG. 28B. A long bone 540 is shown having a fracture 542. Threads are made on the internal surfaces of bone 540 in the appropriate positions in the manner previously described. Component 502 is then positioned within the upper section 540a of bone 540 by engaging outer threaded surface 506 into the threaded position in section 540a to fix component 502 in its proper location. Component 512 is then positioned onto threaded portion 510 of cylindrical portion 508 while component 512 is being threaded into lower section 540b of bone 540. Component 512 is rotated until it is firmly coupled to both component 502 and bone 540. In this embodiment, left handed threads may be used for threaded 510 and also for threaded outer surface 514 and threaded aperture 516. In this manner, the action of installing component 502 of device 500 acts to pull the components together. After device 500 has been installed in bone 540, holes may be drilled into upper section 540a and lower section 540b through the upper and lower ends of component 502 and screws 520 inserted to prevent rotation of long bone 540 about device 500.

FIG. 28C shows device 500 installed within long bone 540 without the use of screws 520.

Another embodiment for use with the arthroplasty devices according to the present invention involves the use of bone cells. Bone and bone cells are grown onto the prosthesis prior to implanting the device into a patient. To accomplish this task, bone cells are initially harvested from a patient. Osteoblasts could be harvested from a patient's iliac crest; a piece of iliac crest bone could be surgically removed. In "Culture of Animal Cells" by R. Ian Freshney, Wiley-Liss New York 2000, which is incorporated herein by reference, techniques for harvesting osteoblasts are described on pps. 370–372. Also described in the article are cell culture techniques. U.S. Pat. No. 6,544,290, which issued on Apr. 8, 2003, to Lee et al, which patent is hereby incorporated by reference, teaches a method culturing cells onto a resorbing calcium phosphate material. The present invention contemplates the culturing of cells onto arthroplasty devices made of titanium, chrome, cobalt, ceramic, or other non-resorbable materials.

In the present invention, bone is harvested from a patient, and the bone then treated to remove the cells. The cells are cultured and grown onto the prosthesis in a lab. The device, now covered with living bone cells, is subsequently implanted into the patient. These cells, which include osteoblasts, osteocytes, donor bone cells, stem cells or other pluripotential cells, and other cells that are capable of transforming into osteoblasts or osteocytes, will promote the bone ingrowth to improve the stability of the device in the body. Alternatively, the bone cells could be added to the device at the time of surgery.

To foster the improved bone ingrowth, the titanium components would have surface treatments. For example, the surfaces could be porous, beaded, plasma sprayed, or covered with fibrillar wire to promote ingrowth. Alternatively, the cells could be cultured onto arthroplasty devices made of other metals, or materials such as ceramic and hydroxyapatite coated metals. In addition, to attempt to improve the ingrowth characteristics of this process, bone growth promoting substances such as TGF-$\alpha$,-$\beta 1$, -2; EGF, IGF-I; PDGF, FGF, BMP-1, VEGF and other similar substances may be added to the cell culture medium.

It is contemplated that features of the various embodiments may be combined. For example, the expandable component taught in FIGS. 8A–B could be used with the threaded component of FIGS. 2–7. Also, although the drawings are directed primarily to the use of the invention in prosthetic hips, the principles may be applied to other prosthetic joints, such as knees, shoulders, ankles and wrists. In addition, bone cells harvested from the patient could be added to the bone growth promoting substance used in other embodiments. These cells could also be combined with a cell culture media or a synthetic matrix.

While the present invention has been shown and described in terms of preferred embodiments thereof, it will be understood that this invention is not limited to any particular embodiment, and that changes and modifications may be made without departing from the true spirit and scope of the invention as defined in the appended claims.

What is claimed is:

1. A prosthesis for implantation into a bone, comprising:
   a sleeve having an inner passageway containing a central opening with at least one channel located on the periphery of said central opening, and an outer surface, sized to fit tightly within the bone, containing at least one section contacting the bone, said section having a textured surface to promote bone ingrowth;
   and a rod component comprising an elongated shank having an outer surface extending between a proximal end and a relatively narrow distal end, with at least a portion of said shank having at least one lobe extending therefrom, said portion of said shank sized to fit within said inner passageway of said sleeve;
   wherein when said rod component is inserted through said sleeve which has been inserted tightly into the bone, the interaction between said lobe of said shank of said rod component and said channel within said sleeve allow for a small amount of rotation, thus reducing torsional shear stress between said prosthesis and the bone.

2. The device of claim 1 wherein said textured surface comprises an array of beads.

3. The device of claim 1 wherein said textured surface comprises an array of fibrillar wires.

4. The device of claim 1, wherein said rod component contains a collar stop for contacting said sleeve.

5. The device of claim 1, wherein said sleeve contains a plurality of channels on the periphery of said central opening and said rod component contains a plurality of lobes along at least a portion of said shank corresponding to each channel.

6. The device of claim 5, wherein the cross section of at least a portion of said sleeve and said rod component form complementary cruciform shapes.

7. The device of claim 1, wherein said bone contacting section of said sleeve contains a bone growth promoting material.

8. The device of claim 7, wherein said bone growth promoting material comprises bone morphogenetic protein (BMP).

9. The device of claim 7, wherein said bone growth promoting material comprises platelet rich plasma.

10. The device of claim 1, wherein said device contains a rod component having varying degrees of version.

11. The device of claim 10, wherein said version comprises antiversion.

12. The device of claim 10, wherein said version comprises retroversion.

* * * * *